US007966066B2

(12) United States Patent
Yu et al.

(10) Patent No.: US 7,966,066 B2
(45) Date of Patent: Jun. 21, 2011

(54) APPARATUS AND METHOD FOR OPTIMIZING ATRIOVENTRICULAR DELAY

(75) Inventors: Yinghong Yu, Shoreview, MN (US); Jiang Ding, Maplewood, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 707 days.

(21) Appl. No.: 11/126,490

(22) Filed: May 11, 2005

(65) Prior Publication Data

US 2006/0259086 A1    Nov. 16, 2006

(51) Int. Cl.
*A61N 1/362* (2006.01)
(52) U.S. Cl. ......... 607/9; 607/1; 607/2; 607/11; 607/17; 607/115
(58) Field of Classification Search .................. 607/1–2, 607/9, 11, 17, 115
See application file for complete search history.

(56) References Cited

U.S. PATENT DOCUMENTS

| 5,507,782 | A | 4/1996 | Kieval et al. | |
|---|---|---|---|---|
| 6,144,880 | A | 11/2000 | Ding et al. | |
| 6,351,673 | B1 | 2/2002 | Ding et al. | |
| 6,360,127 | B1 | 3/2002 | Ding et al. | |
| 6,473,645 | B1 * | 10/2002 | Levine | 607/9 |
| 6,498,950 | B1 | 12/2002 | Bradley | |
| 6,665,564 | B2 * | 12/2003 | Lincoln et al. | 607/17 |
| 7,184,835 | B2 * | 2/2007 | Kramer et al. | 607/9 |
| 2003/0018363 | A1 | 1/2003 | Ding et al. | |
| 2003/0144702 | A1 | 7/2003 | Yu et al. | |
| 2003/0144703 | A1 | 7/2003 | Yu et al. | |
| 2004/0049236 | A1 * | 3/2004 | Kramer et al. | 607/9 |
| 2004/0147966 | A1 | 7/2004 | Ding et al. | |
| 2004/0172081 | A1 | 9/2004 | Wang | |

FOREIGN PATENT DOCUMENTS

WO     WO-2006122219 A1    11/2006

OTHER PUBLICATIONS

Auricchio et al., Cardiac Resynchronization Therapy Restores Optimal Atrioventricular Mechanical Timing in Heart Failure Patients with Ventricular Conduction Delay, *Journal of the American College of Cardiology*, vol. 39, No. 7, pp. 1163-1169 (Apr. 3, 2002).
"International Search Report and Written Opinion for Application No. PCT/US2006/018162, Date mailed October 10, 2006", 12 pages.

* cited by examiner

*Primary Examiner* — Carl H Layno
*Assistant Examiner* — Deborah Malamud
(74) *Attorney, Agent, or Firm* — Schwegman, Lundberg & Woessner, P.A.

(57) ABSTRACT

Systems and methods to optimize atrioventricular delay during sensing or pacing of the atrium and for a plurality of sensed rates or pacing rates. In one example, a paced atrioventricular delay is calculated using a sensed atrioventricular interval and a paced atrioventricular interval. In another example, a plurality of paced atrioventricular delays for different pacing rates can be calculated. In another example embodiment, a plurality of sensed atrioventricular delays for different sensing rates can be calculated. Combinations of the various systems and methods are also possible.

10 Claims, 10 Drawing Sheets

APPARATUS AND METHOD FOR OPTIMIZING ATRIOVENTRICULAR DELAY

TECHNICAL FIELD

The present invention is directed to cardiac resynchronization therapy systems. More specifically, the present invention is directed to systems and methods to optimize atrioventricular delay during cardiac resynchronization therapy.

BACKGROUND

Figure 1:
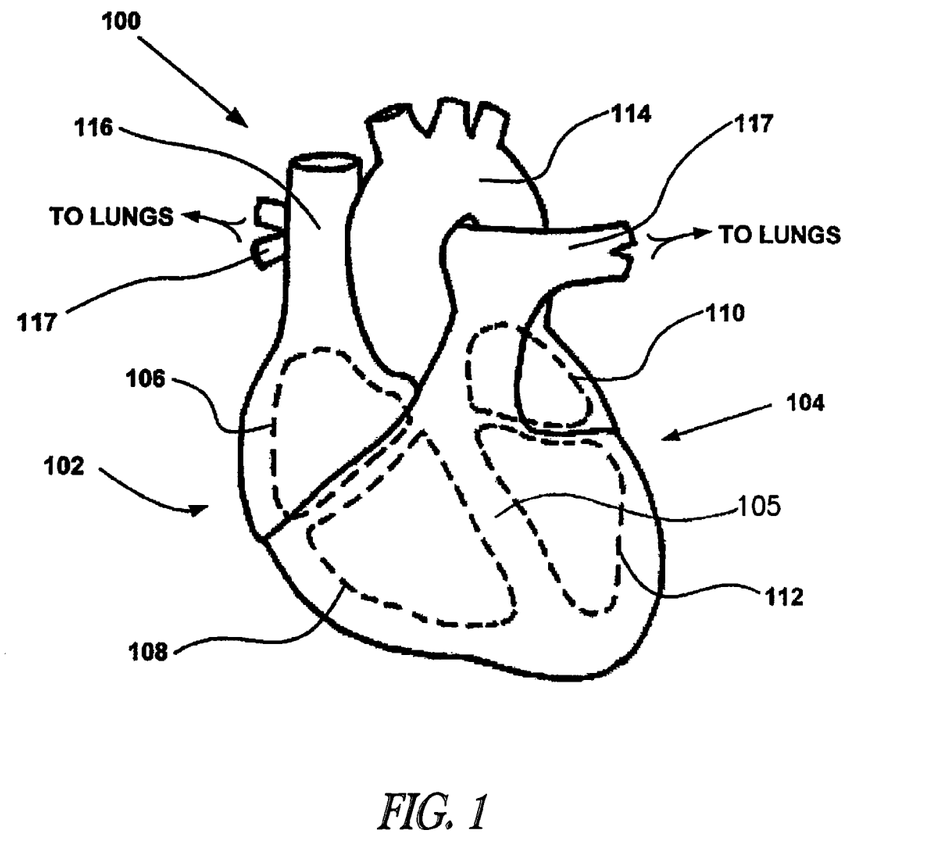
FIG. 1 is a simplified illustration depicting primary pumping components of a human heart.

The heart is a muscular organ comprising multiple chambers that operate in concert to circulate blood throughout the body's circulatory system. As shown in FIG. 1, the heart 100 includes a right-side portion or pump 102 and a left-side portion or pump 104. The right-side portion 102 includes a right atrium 106 and a right ventricle 108. Similarly, the left-side portion 104 includes a left atrium 110 and a left ventricle 112 separated by an interventricular septum 105. Oxygen-depleted blood returning to the heart 100 from the body collects in the right atrium 106. When the right atrium 106 fills, the oxygen-depleted blood passes into the right ventricle 108 where it can be pumped to the lungs (not shown) via the pulmonary arteries 117.

Within the lungs, waste products such as carbon dioxide are removed from the blood and expelled from the body and oxygen is transferred to the blood. Oxygen-rich blood returning to the heart 100 from the lungs via the pulmonary veins (not shown) collects in the left atrium 110. The circuit between the right-side portion 102, the lungs, and the left atrium 110 is generally referred to as the pulmonary circulation. After the left atrium 110 fills, the oxygen-rich blood passes into the left ventricle 112 where it can be pumped throughout the entire body. In so doing, the heart 100 is able to supply oxygen to the body and facilitate the removal of waste products from the body.

To circulate blood throughout the body's circulatory system as described above, a beating heart performs a cardiac cycle that includes a systolic phase and a diastolic phase. During the systolic phase, or systole, the ventricular muscle cells of the right and left ventricles 108 and 112 contract to pump blood through the pulmonary circulation and throughout the body, respectively. Conversely, during the diastolic phase, or diastole, the ventricular muscle cells of the right and left ventricles 108 and 112 relax, during which the right and left atriums 106 and 110 contract to force blood into the right and left ventricles 108 and 112, respectively. Typically, the cardiac cycle occurs at a frequency between 60 and 100 cycles per minute and can vary depending on physical exertion and/or emotional stimuli, such as pain or anger.

Figure 2:
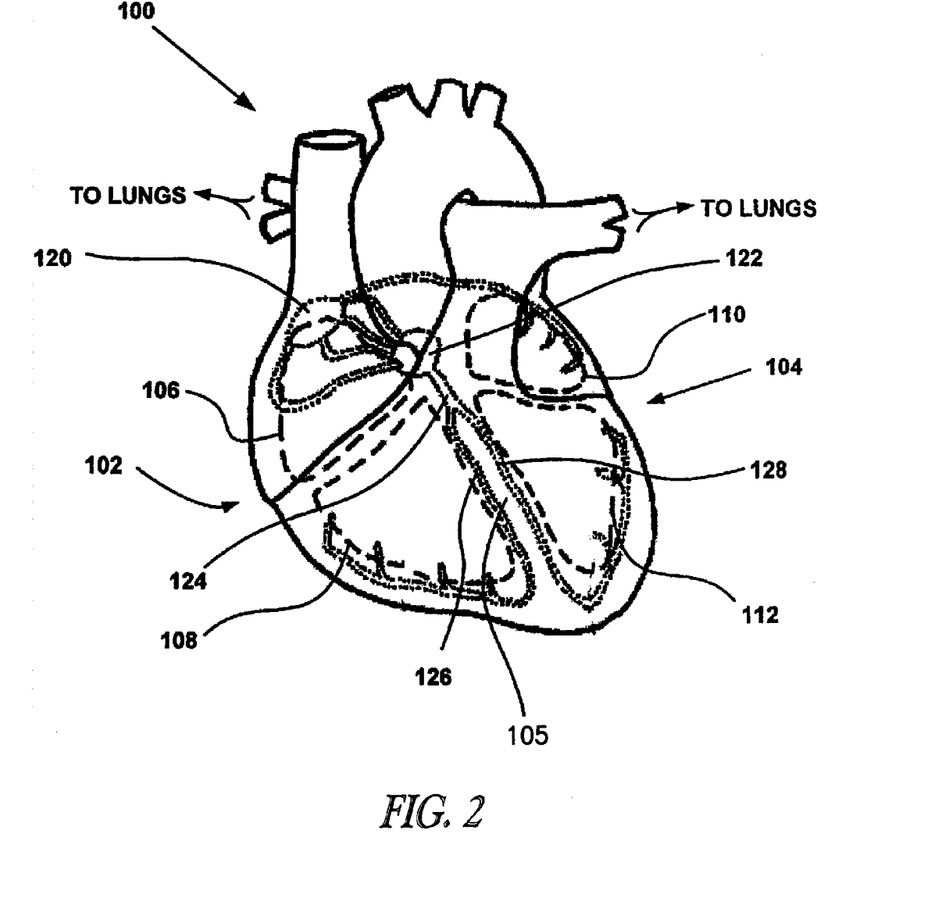
FIG. 2 is a simplified illustration depicting a human heart and the transmission paths over which a normal heart provides depolarization waves to the heart chambers.

The contractions of the muscular walls of each chamber of the heart 100 are controlled by a complex conduction system that propagates electrical signals to the heart muscle tissue to effectuate the atrial and ventricular contractions necessary to circulate the blood. As shown in FIG. 2, the complex conduction system includes an atrial node 120 (the sinoatrial node) and a ventricular node 122 (the atrioventricular node). The sinoatrial node 120 initiates an electrical impulse that spreads through the muscle tissues of the right and left atriums 106 and 110 and the atrioventricular node 122. As a result, the right and left atriums 106 and 110 contract to pump blood into the right and left ventricles 108 and 112, as discussed above.

At the atrioventricular node 122, the electrical signal is momentarily delayed before propagating through the right and left ventricles 108 and 112. Within the right and left ventricles 108 and 112, the conduction system includes right and left bundle branches 126 and 128 that extend from the atrioventricular node 122 via the Bundle of His 124. The electrical impulse spreads through the muscle tissues of the right and left ventricles 108 and 112 via the right and left bundle branches 126 and 128, respectively. As a result, the right and left ventricles 108, 112 contract to pump blood throughout the body as discussed above.

Normally, the muscular walls of each chamber of the heart 100 contract synchronously in a precise sequence to efficiently circulate the blood as described above. In particular, both the right and left atriums 106 and 110 contract and relax synchronously. Shortly after the atrial contractions, both the right and left ventricles 108 and 112 contract and relax synchronously. Several disorders or arrhythmias of the heart can prevent the heart from operating normally, such as, blockage of the conduction system, heart disease (e.g., coronary artery disease), abnormal heart valve function, or heart failure.

Blockage in the conduction system can cause a slight or severe delay in the electrical impulses propagating through the atrioventricular node 122, causing inadequate ventricular contraction, relaxation, and filling. In situations where the blockage is in the ventricles (e.g., the right and left bundle branches 126 and 128), the right and/or left ventricles 108 and 112 can only be excited through slow muscle tissue conduction. As a result, the muscular walls of the affected ventricle (108 and/or 112) do not contract synchronously (known as asynchronous contraction), thereby reducing the overall effectiveness of the heart 100 to pump oxygen-rich blood throughout the body.

Various medical procedures have been developed to address heart disorders. In particular, cardiac resynchronization therapy ("CRT") can be used to improve the conduction pattern and sequence of the heart 100. CRT involves the use of an artificial electrical stimulator that is surgically implanted within the patient's body. Leads from the stimulator can be affixed at a desired location within the heart 100 to effectuate synchronous atrial and/or ventricular contractions. Typically, the location of the leads, or the stimulation site, is selected based upon the severity and/or location of the blockage. Electrical stimulation signals can be delivered to resynchronize the heart, thereby improving cardiac performance.

One important parameter associated with CRT is atrioventricular delay or "AV delay," which is the programmed time interval between a paced or sensed atrial event and the corresponding paced or sensed ventricular event. Referring to FIGS. 3-7, an example timeline and method are shown for calculating an AV delay.

Figure 3:
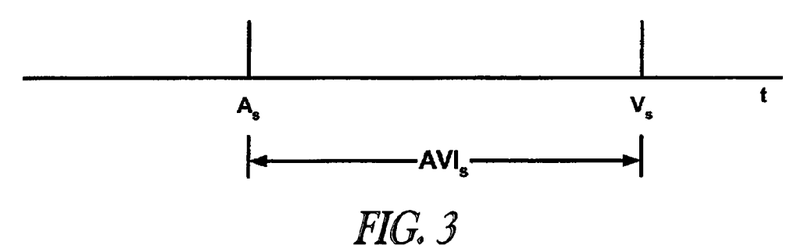
FIG. 3 is a timeline illustrating an example atrioventricular interval between sensed atrial and ventricle activity.

Referring to FIG. 3, a specific instant in atrial ("A") and ventricle ("V") activity is illustrated. For example, the sensing of atrial ("$A_s$") activity and sensing of ventricle ("$V_s$") activity during intrinsic heart activity is shown for a single heartbeat. The time $A_s$ represents when atrial depolarization (or electrical activation) is sensed. The time $V_s$ represents when ventricular depolarization is sensed. The interval between $A_s$ and $V_s$ is the sensed atrioventricular interval ("$AVI_s$").

Figure 4:
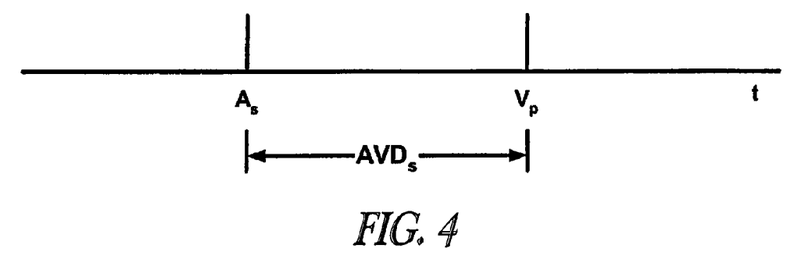
FIG. 4 is a timeline illustrating an example calculated optimized atrioventricular delay for sensed atrial and paced ventricular activity.

The $AVI_s$ can be used to calculate an optimal AV delay for ventricular pacing during intrinsic or sensed atrial contraction ("$AVD_s$"), as shown in FIG. 4, using various techniques. For example, methods described in U.S. Pat. No. 6,144,880 to Ding et al. and U.S. patent application Ser. Nos. 10/314,899 and 10/314,910 to Yu et al., all of which are hereby incorporated by reference in their entireties, can be used to calculate $AVD_s$ from $AVI_s$. Equation 1 below generally illustrates one possible relationship between $AVI_s$ and an optimized $AVD_s$.

$$AVD_s = K1(AVI_s) - K2 \qquad (1)$$

The constants K1 and K2 may vary depending on the interval measured and patient diversity. See U.S. Pat. No. 6,144,880.

In another example, U.S. patent application Ser. No. 10/352,780 to Ding et al., which is hereby incorporate by reference, describes methods for calculating optimal $AVD_S$. For example, the following equation can be used to calculate an optimal $AVD_s$: $AVD_s=k_1AV_{Rs}+k_2AV_{Ls}$, where $AV_{Rs}$ is the interval between atrial sense and right ventricular sense, and $AV_{Ls}$ is the interval between atrial sense and left ventricular sense.

Figure 5:
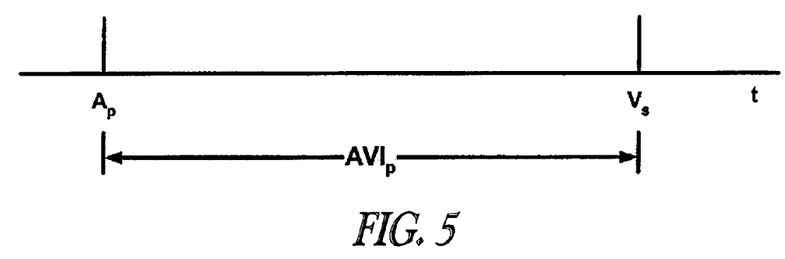
FIG. 5 is a timeline illustrating an example atrioventricular interval between paced atrial and sensed ventricle activity.

Referring now to FIG. 5, an embodiment in which the atrium is paced ("$A_p$") is illustrated. $A_p$ represents the introduction of an electrical impulse to the atrium, and, as previously noted, $V_s$ represents sensing of intrinsic ventricular activity. The interval between $A_p$ and $V_s$ is the atrioventricular interval during atrial pacing and ventricular sensing ("$AVI_p$").

Figure 6:
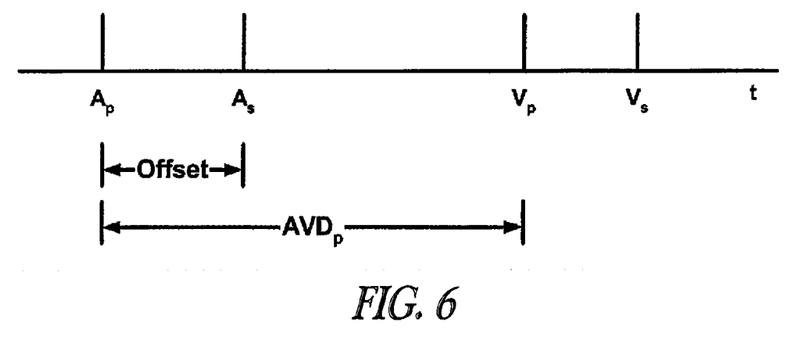
FIG. 6 is a timeline illustrating an example offset and an example calculated optimized atrioventricular delay for paced atrial and paced ventricular activity.

As shown in FIG. 6, a difference between $AVI_s$ and $AVI_p$, labeled as the offset, can be calculated using Equation 2.

$$\text{offset}=AVI_p-AVI_s \quad (2)$$

Using this offset, the optimal atrioventricular delay for atrial and ventricular pacing ("$AVD_p$") can be calculated using Equation 3.

$$AVD_p=AVD_s+\text{offset} \quad (3)$$

Figure 7:
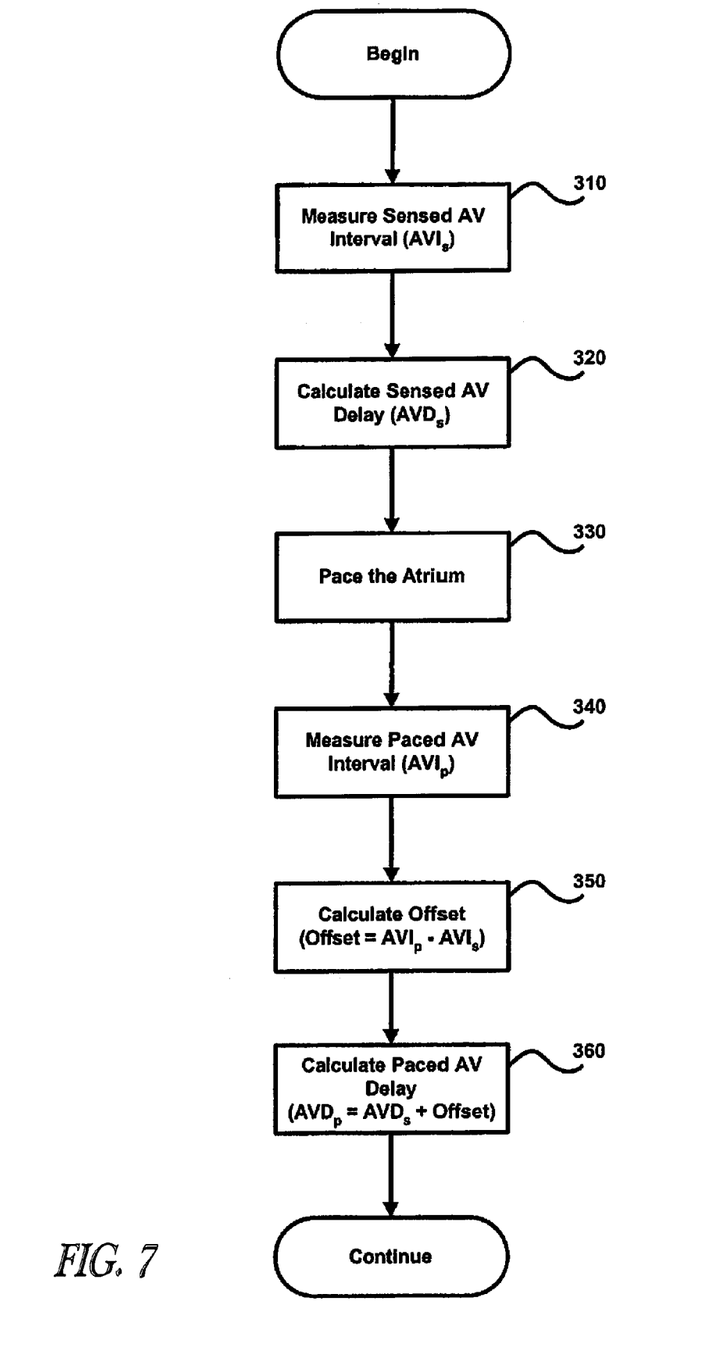
FIG. 7 is an example flow diagram for calculating an atrioventricular delay.

Referring now to FIG. 7, using Equations 2 and 3 described above, an example method is shown to calculate the $AVD_p$ for a CRT device. In operation 310, the $AVI_s$ is measured by the CRT device. In operation 320, the optimal $AVD_s$ for sensed atrium and paced ventricle is calculated as described above. Then, in operation 330, the atrium is paced for one or more beats. In operation 340, the $AVI_p$ is measured. Next, the offset is calculated in operation 350 using Equation 2 above. Finally, in operation 360, the optimal $AVD_p$ for paced atrium and paced ventricle can be calculated using Equation 3.

Other methods can also be used to calculate an optimized $AVD_p$. For example, U.S. patent application Ser. No. 10/243,811 to Ding et al., which is hereby incorporated by reference in its entirety, describes a method to calculate $AVD_p$ using $AVI_p$, according to the following Equation 4.

$$AVD_p=K1(AVI_p)-K2 \quad (4)$$

The above example methods illustrated in Equations 1-4 allow for the calculation of $AVD_s$ or $AVD_p$ using a fixed atrial sensing or pacing rate. A typical pacing system uses a standard pre-set AV delay when pacing a heart. Therefore, prior art systems do not account for changes in atrioventricular delays associated with changes in heart rate or pacing rate, or changes in the mode in which the heart is being paced (e.g., changes from atrial sensing to atrial pacing).

However, optimal AV delays can vary depending on the rate of pacing and on whether the atrium is being sensed or paced. For example, as illustrated in FIGS. 4 and 6, $AVD_s$ is usually shorter than $AVD_p$ because when pacing the right atrium, activation of the left atrium is further delayed. In order to maintain the appropriate contraction sequence of the left atrium and ventricle, the timing of left ventricular stimulation needs to be delayed correspondingly, which necessitates a longer $AVD_p$.

The AV delay can have a significant impact on the hemodynamic efficiency of the heart 100. AV delays of greater than or less than optimal length can cause asynchronous contraction, which can result in less oxygen-rich blood being pumped during each stroke of the heart 100.

Therefore, there is a need for systems and methods that can efficiently and accurately optimize AV delay, and utilize these AV delays at different sensing and pacing rates and during different pacing modes (e.g., atrial sensing or atrial pacing).

SUMMARY

The present invention is directed to cardiac resynchronization therapy systems. More specifically, the present invention is directed to systems and methods to optimize atrioventricular delay during cardiac resynchronization therapy.

According to one aspect, embodiments of the invention relate to a cardiac resynchronization device associated with a heart, the cardiac resynchronization device including a therapy module for delivering resynchronization therapy to the heart, and a sensing module and a timer module capable of sensing and timing a plurality of atrioventricular intervals at a plurality of rates. The device also includes a controller coupled to the timer module capable of calculating a plurality of atrioventricular delays for resynchronization therapy based on the plurality of atrioventricular intervals, and a memory module capable of storing the plurality of atrioventricular delays.

According to another aspect, embodiments of the invention relate to method for optimizing atrioventricular delay for a cardiac resynchronization device, including: measuring a plurality of atrioventricular intervals of a heart at a plurality of rates; calculating an atrioventricular delay for each of the plurality of atrioventricular intervals; and storing the atrioventricular delay for each of the plurality of atrioventricular intervals in a memory of the cardiac resynchronization device.

According to yet another aspect, embodiments of the invention relate to a method for optimizing atrioventricular delay for a cardiac resynchronization device, including: pacing a heart at a first rate; measuring a first atrioventricular interval; calculating a first atrioventricular delay; storing the first atrioventricular delay in a lookup table in a memory of the cardiac resynchronization device; pacing the heart at a second rate greater than the first rate; measuring a second atrioventricular interval; calculating a second atrioventricular delay; and storing the second atrioventricular delay in the lookup table in the memory of the cardiac resynchronization device.

According to another aspect, embodiments of the invention relate to a method for optimizing atrioventricular delay for cardiac resynchronization therapy, including: measuring a first atrioventricular interval at a first pacing rate, the first atrioventricular interval spanning a first event corresponding to atrial activity of an atrium and a second event corresponding to ventricular activity of a ventricle of a heart; calculating a first atrioventricular delay based on the first atrioventricular interval; storing the first atrioventricular delay and the first pacing rate in a lookup table in a memory of a cardiac resynchronization device; measuring a second atrioventricular interval at a second pacing rate; calculating a second atrioventricular delay; and storing the second atrioventricular delay and the second pacing rate in the lookup table in the memory of the cardiac resynchronization device.

According to another aspect, embodiments of the invention relate to a method for optimizing sensed atrioventricular delay for a cardiac resynchronization device, including: measuring a first sensed rate; determining if the first sensed rate exceeds a threshold; and if the first sensed rate exceeds a threshold, determining if a first sensed atrioventricular delay has not been previously calculated or has expired for the first sensed rate. If the first sensed atrioventricular delay has not been previously calculated or has expired: measuring a first sensed atrioventricular interval; calculating the first sensed atrioventricular delay from the first sensed atrioventricular interval; and storing the first sensed atrioventricular delay in a memory of the cardiac resynchronization device.

According to yet another aspect, embodiments of the invention relate to a method for optimizing sensed and paced atrioventricular delays for a cardiac resynchronization device associated with a heart, including: measuring a sensed atrioventricular interval of the heart; pacing an atrium of the heart; measuring a paced atrioventricular interval; and calculating an offset based on the sensed atrioventricular interval and the paced atrioventricular interval.

The above summary is not intended to describe each disclosed embodiment or every implementation of the present invention. The figures and detailed description that follow more particularly exemplify embodiments of the invention. While certain embodiments will be illustrated and described, the invention is not limited to use in such embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention generally relates to cardiac resynchronization therapy systems. More specifically, the present invention is directed to systems and methods to optimize atrioventricular delay during cardiac resynchronization therapy.

As used herein, the terms "intrinsic" and "sensed" mean the natural or unprovoked activity of the heart such as, for example, depolarization of the heart. The term "paced" is used herein to mean stimulation of the heart caused by one or more electrical impulses delivered to the heart by, for example, a cardiac rhythm management ("CRM") system including a cardiac resynchronization therapy ("CRT") device.

In addition, the term "atrioventricular interval," whether sensed or paced, means an interval between an identifiable portion of atrial electrical activity and an identifiable portion of ventricular electrical activity. This interval can be measured using various methods. For example, the interval $AQ_s^*$ or $AQ_p^*$ (the interval between a sensed or paced atrial event and the onset of the ventricular electrical event) or $AVI_s$ or $AVI_p$ (the interval between a sensed or paced atrial event and a sensed ventricular electrical event) can be used to measure the atrioventricular interval. See, for example, U.S. Pat. No. 6,144,880 to Ding et al. and U.S. patent application Ser. Nos. 10/314,899 and 10/314,910 both to Yu et al. for example methods for measuring the atrioventricular interval.

Embodiments of the present invention can be used to optimize atrioventricular ("AV") delay ("AVD") during sensing or pacing of the atrium and for a plurality of pacing rates. In one example embodiment, a plurality of paced AV delays for different rates can be calculated. In another example embodiment, a plurality of sensed AV delays for different sensing rates can be calculated. In another embodiment, a plurality of sensed AV delays for different sensing rates are converted from paced AV delays calculated at different pacing rates. In other embodiments, the sensed AV delays for different sensing rates are calculated and populated as needed. Combinations of the various embodiments are also possible.

The present systems and methods are described with respect to implantable CRM systems, such as pacemakers, cardioverter/defibrillators, pacer/defibrillators, and multi-chamber and/or multi-site (in a single or multiple heart chambers) CRT devices. Such CRT devices are included within CRM systems even though the CRT devices need not necessarily modulate heart rate. Such CRT devices may instead provide contraction-evoking stimulations that establish or modify the conduction path of propagating depolarizations to obtain more efficient pumping of the heart. Moreover, the present systems and methods also find application in other implantable medical devices, and in unimplanted ("external") devices, including, but not limited to, external pacemakers, cardioverter/defibrillators, pacer/defibrillators, multi-chamber and/or multi-site CRT devices, monitors, programmers, and recorders, whether such devices are used for providing a diagnostic, a therapy, or both.

The methods disclosed herein may be manually implemented by, for example, a caregiver. Alternatively, the CRT device may automatically perform one or more of the methods. The CRT device may perform one or more of the methods subsequent to implantation and prior to delivery of therapy. In addition, the CRT device may perform one or more of the methods at selected or periodic intervals in order to re-optimize operating parameters.

I. System

Figure 8:
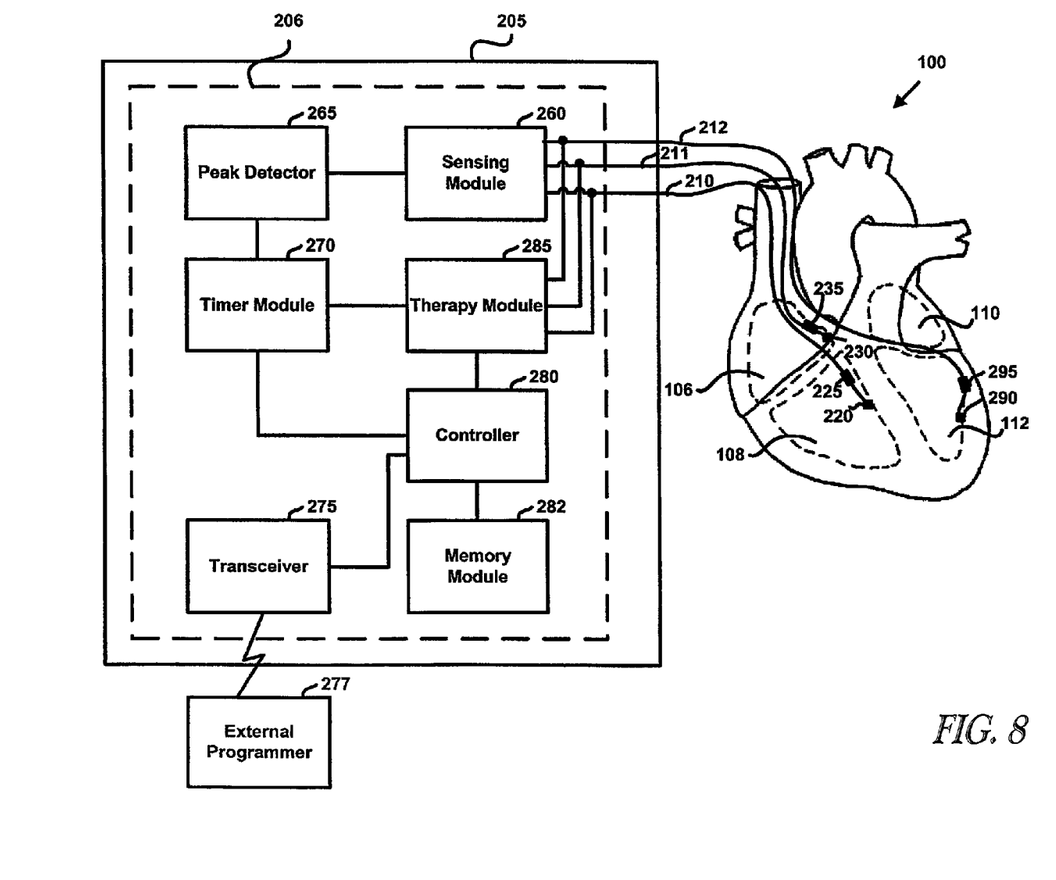
FIG. 8 is a schematic/plan drawing of an example embodiment of a cardiac rhythm management system coupled to a human heart.

Referring now to FIG. 8, one embodiment illustrating various components of a CRM system 205 is shown along with the heart 100. In this embodiment, the CRM system 205 includes, among other elements, CRT device 206, which is coupled by leads 210, 211, and 212 to the heart 100. Lead 210 is positioned in the right ventricle, lead 211 positioned in the right atrium, and lead 212 positioned on the left ventricle.

In one embodiment, leads 210, 211, and 212 include electrodes 220, 230, and 290 associated with the right ventricle, right atrium, and left ventricle, respectively. Each electrode is "associated" with the particular heart chamber by inserting it into that heart chamber, or by inserting it into a portion of the heart's vasculature that is close to that heart chamber, or by epicardially placing the electrode outside that heart chamber, or by any other technique of configuring and situating an electrode for sensing signals and/or providing therapy with respect to that heart chamber. Leads 210, 211, and 212 may alternatively also include ring electrodes 225, 235, and 295. Each electrode may be used for unipolar sensing of heart signals and/or unipolar delivery of contraction-evoking stimulations in conjunction with one or more other electrodes associated with the heart 100. Alternatively, bipolar sensing and/or therapy may be delivered, for example, between electrodes 220 and 225 of lead 210.

The CRT device 206 includes a sensing module 260, which is coupled to one or more of the electrodes for sensing electrical depolarizations corresponding to heart chamber activity. Such electrical depolarizations of the heart tissue include atrial depolarizations, referred to as P-waves, and ventricular depolarizations, referred to as QRS complexes. The QRS complex is a rapid sequence of several signal excursions away from a baseline in sequentially switching polarity, with the largest excursion referred to as an R-wave.

A peak detector 265 is coupled to the sensing module 260 for detecting, for example, the P-wave peak from the right atrium 106, obtained by bipolar sensing between electrodes 230 and 235, or by any other sensing technique. Peak detector 265 may also sense the R-wave peak at a plurality of different sites associated with the left ventricle 112 or right ventricle 108, such as at each of the electrodes 290 and 295. Sensing may be unipolar or bipolar. The peak detector 265 may detect a variety of points associated with the electrical activity of the heart 100.

A timer module 270 is coupled to the peak detector 265 for timing one or more intervals between one or more events. For example, the timer module 270 may be used to time an interval between atrial and ventricular activity. As previously described, this interval is known as the atrioventricular ("AV") interval ("AVI"). Because the interval is measured during sensing of the atrium and ventricle, the interval is referred to herein as the sensed atrioventricular interval ("$AVI_s$"). The timer module 270 is also coupled to the therapy module 285, which provides the time at which an atrial stimulation is delivered. Thus, timer module 270 can also measure the interval between an atrial pacing impulse and sensed ventricular activity ("$AVI_p$").

A controller 280 is coupled to the timer module 270. The controller 280 may process the one or more intervals measured by the timer module 270. For example, the controller 280 may implement one or more of the methods described in sections II-IV below. The controller 280 may store one or more calculations in a memory module 282 coupled to the controller 280.

A therapy module 285 is coupled to the controller 280. The controller 280 controls the therapy module 285, and the therapy module 285 is configured to deliver electrical impulses to the heart 100 by leads 210, 211, and/or 212. The electrical impulses may be used to stimulate activity (e.g., contraction) in one or more chambers of the heart.

The CRM system 205 also includes a telemetry transceiver 275, which is communicatively coupled to an external programmer 277. The external programmer 277 may remotely communicate with the telemetry transceiver 275 to, for example, extract data from or reprogram the CRM system 205. In the example embodiments of the present invention, the external programmer 277 is used to control the mode and pacing of the CRM system 205.

The CRT device 206 may operate in a variety of modes. In a first mode, VDD, the atrium 106 is sensed and one or both of the ventricles 108 and 112 are paced. In a second mode, DDD, both the atrium 106 and one or both of the ventricles 108 and 112 are paced. A switch between VDD and DDD pacing is referred to as a mode switch.

As described by one or more of the methods below, this invention relates to methods to calculate optimized sensed and/or paced AV delays at a plurality of rates. In addition, methods are provided to allow for switching to different modes (e.g., between atrial sensing and pacing) at different paced and sensed rates.

II. Optimization of Paced AV Delay for a Plurality of Atrial Pacing Rates

In accordance with an example embodiment of the invention, the paced atrioventricular delay ("$AVD_p$") for a plurality of pacing rates may be optimized when a CRT device is operating in a paced atrial mode (e.g., DDD mode) using one or more of the methods described below.

Figure 9:
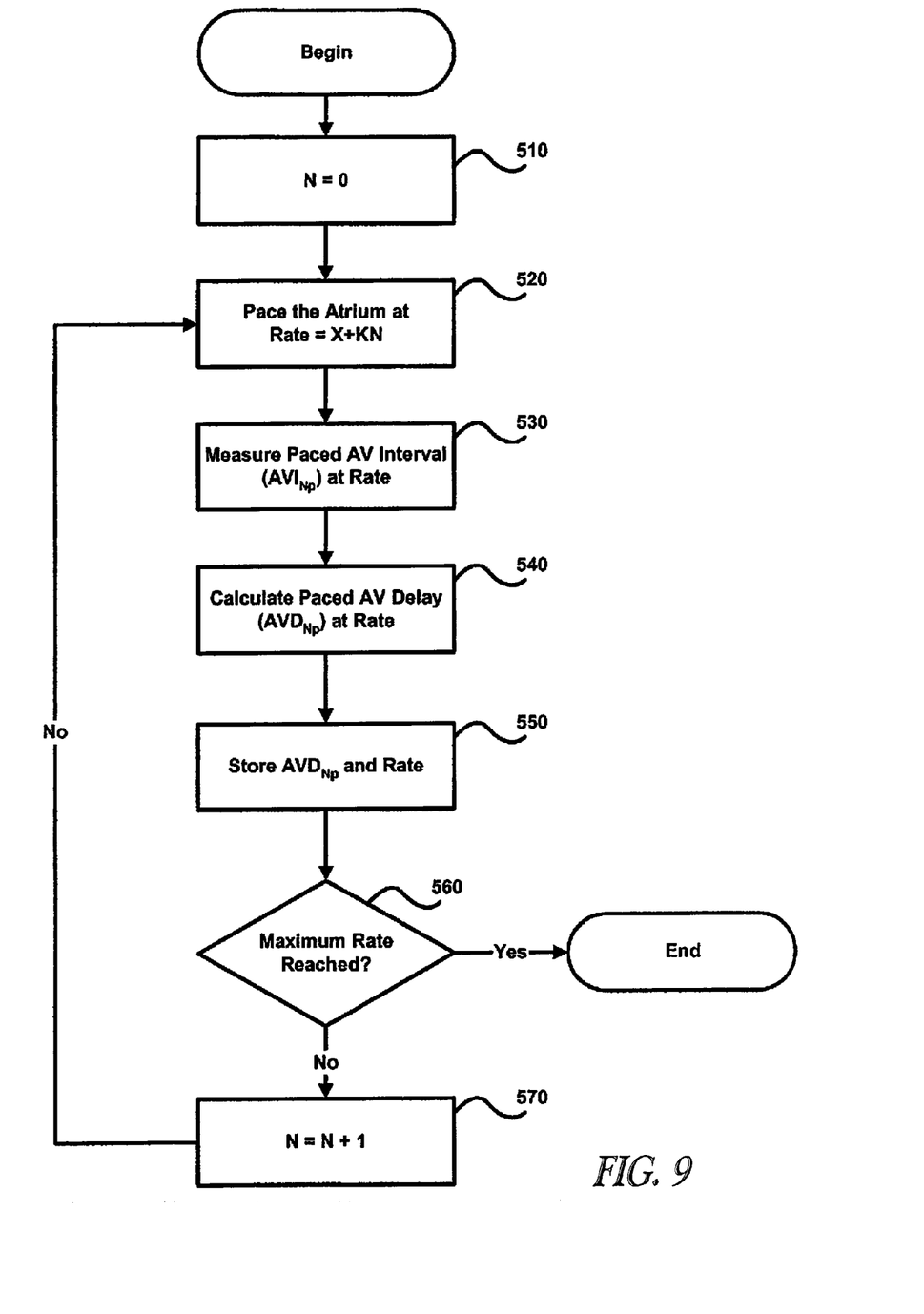
FIG. 9 is an example flow diagram for calculating a plurality of optimized atrioventricular delays for a paced atrium at a plurality of pacing rates.

For example, one example method for calculating a plurality of $AVD_p$ at a plurality of pacing rates is shown in FIG. 9. In operation 510, a variable N is set equal to zero. As described below, the variable N is used to increment the pacing rate. In operation 520, the atrium is paced at a rate that is incremented according to Equation 5.

$$\text{Pacing Rate} = X + KN \qquad (5)$$

The variable X is the resting heart rate or lowest desired heart rate of the individual. K is a constant used to control the steps taken between adjacent $AVI_p$ readings. For example, in one embodiment, the constant K is set at 5, so that the pacing rate is incremented by 5 beats for each measured $AVI_p$. Other constants may also be used. For example, K can be set equal to 1 if it is desirable to measure the $AVI_p$ for each pacing rate or may be increased to greater than 5 if less readings are desired.

With N set equal to 1 for the first loop of the method, the heart is paced at a rate of X+K. Next, in operation 530, the $AVI_p$ for the given pacing rate ("$AVI_{Np}$") is measured. Next, in operation 540, the $AVD_p$ for the given pacing rate ("$AVD_{Np}$") is calculated. The $AVD_{Np}$ may be calculated using, for example, an equation similar to Equation 4 described above.

Once the $AVD_{Np}$ is calculated, the $AVD_{Np}$ and associated pacing rate are stored in CRT device memory in operation 550. Then, in operation 560, the current pacing rate is compared to a maximum pacing rate. This maximum pacing rate may be set to any desired value, such as, for example, 180 beats/minute. If the current pacing rate meets or exceeds the maximum rate, the measurements are complete. If the maximum rate has not been reached, in operation 570 the variable N is incremented and control is passed back to operation 520 for a second loop of the method.

During the second loop of the method, the pacing rate is calculated according to Equation 5. A new $AVI_{Np}$ at the new pacing rate is measured in operation 530, and a new $AVD_{Np}$ is calculated in operation 540. The $AVD_{Np}$ and associated pacing rate are also stored in memory in operation 550. The method is continued until the maximum pacing rate is reached.

The $AVD_{Np}$ for each pacing rate that is stored in memory of the CRT device may be assembled in a lookup table similar to Table 1 shown below.

TABLE 1

| Pacing Rate | Optimized $AVD_p$ |
|---|---|
| X + KN | $AVD_{Np}$ |
| X + K(N + 1) | $AVD_{(N+1)p}$ |
| X + K(N + 2) | $AVD_{(N+2)p}$ |
| X + K(N + 3) | $AVD_{(N+3)p}$ |
| X + K(N + 4) | $AVD_{(N+4)p}$ |
| X + K(N + 5) | $AVD_{(N+5)p}$ |

A CRT device may utilize a table such as Table 1 to look up an optimal $AVD_p$ depending on the current atrial pacing rate. As the CRT device pacing rate changes, the CRT device can lookup the appropriate $AVD_p$, thereby maintaining an optimal $AVD_p$ as the pacing rate changes.

III. Optimization of Sensed AV Delay for a Plurality of Sensed Rates

In accordance with other embodiments of the invention, the $AVD_s$ can be optimized for a plurality of sensed heart rates when a CRT device is operating in a sensed atrial mode (e.g., VDD mode). This may be advantageous, for example, for patients exhibiting normal sinus node function but requiring CRT.

Figure 10A:
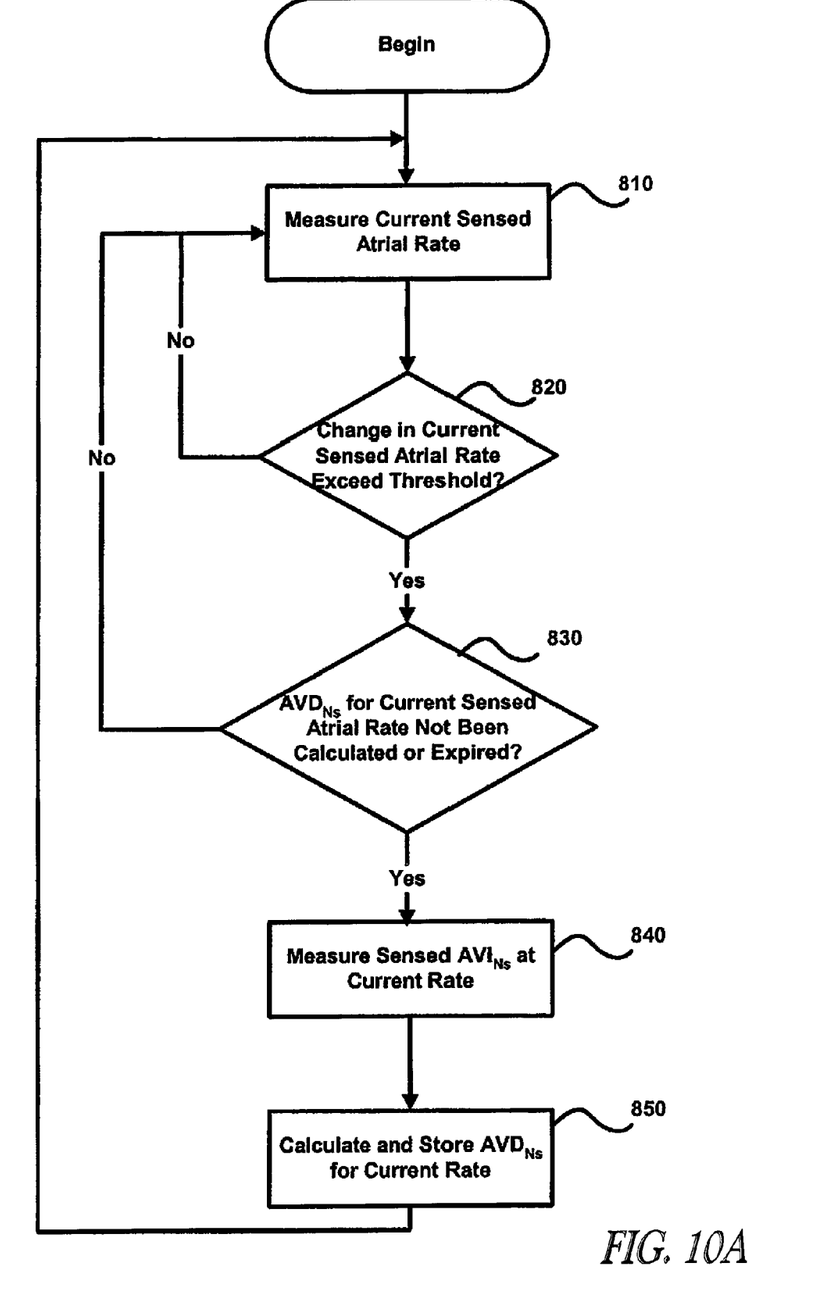
FIG. 10A is an example flow diagram for calculating a plurality of optimized atrioventricular delays for a sensed atrium at a plurality of sensed rates.

For example, a method is illustrated in FIG. 10A for calculating a plurality of different $AVD_s$ at a plurality of sensed heart rates. In operation 810, the current sensed atrial rate is measured. Next, in operation 820, if the current sensed atrial rate has not exceeded the threshold, control is passed back to operation 810. If the current sensed atrial rate has exceed the threshold, control is passed to operation 830, where it is determined whether or not the $AVD_{Ns}$ for the current sensed atrial rate $X_N$ has been previously calculated or is expired.

If the $AVD_{Ns}$ associated with the current sensed atrial rate $X_N$ has not been previously calculated, control is passed to operation 840, and the $AVI_{Ns}$ at the current sensed rate $X_1$ is measured. Next, in operation 850, the $AVD_{Ns}$ for the particular sensed rate is estimated (using, for example, Equation 1 above) and stored, for example, in a table such as Table 2 below.

TABLE 2

| Sensed rate | Optimized $AVD_s$ |
|---|---|
| $X_1$ | $AVD_{1s}$ |
| $X_2$ | $AVD_{2s}$ |
| $X_3$ | $AVD_{3s}$ |
| $X_4$ | $AVD_{4s}$ |
| $X_5$ | $AVD_{5s}$ |
| $X_6$ | $AVD_{6s}$ |

In addition, if the $AVD_{Ns}$ associated with the current sensed atrial rate $X_N$ has been previously calculated but has expired, control is passed to operation 850, where the $AVD_{Ns}$ is recalculated and stored in Table 2. The $AVD_{Ns}$ can be set to expire at a certain interval after calculation such as, for example, one week, one month, two months, etc., so that if the sensed atrial rate is reached after expiration of the interval, the $AVD_{Ns}$ can be recalculated. Control is then passed back to operation 810.

If it is determined in operation 830 that the current sensed atrial rate $X_N$ has been previously calculated and has not expired, control is passed back to operation 810 to continue measuring the current sensed atrial rate.

In this manner, the $AVD_{Ns}$ can be populated in Table 2 as each sensed atrial rate is reached as the patient's heart rate intrinsically fluctuates. Therefore, the values for the $AVD_{Ns}$ are advantageously populated "on the fly." In addition, the values for the $AVD_{Ns}$ can be recalculated at set intervals to account for changes in the patient's condition over time.

Figure 10B:
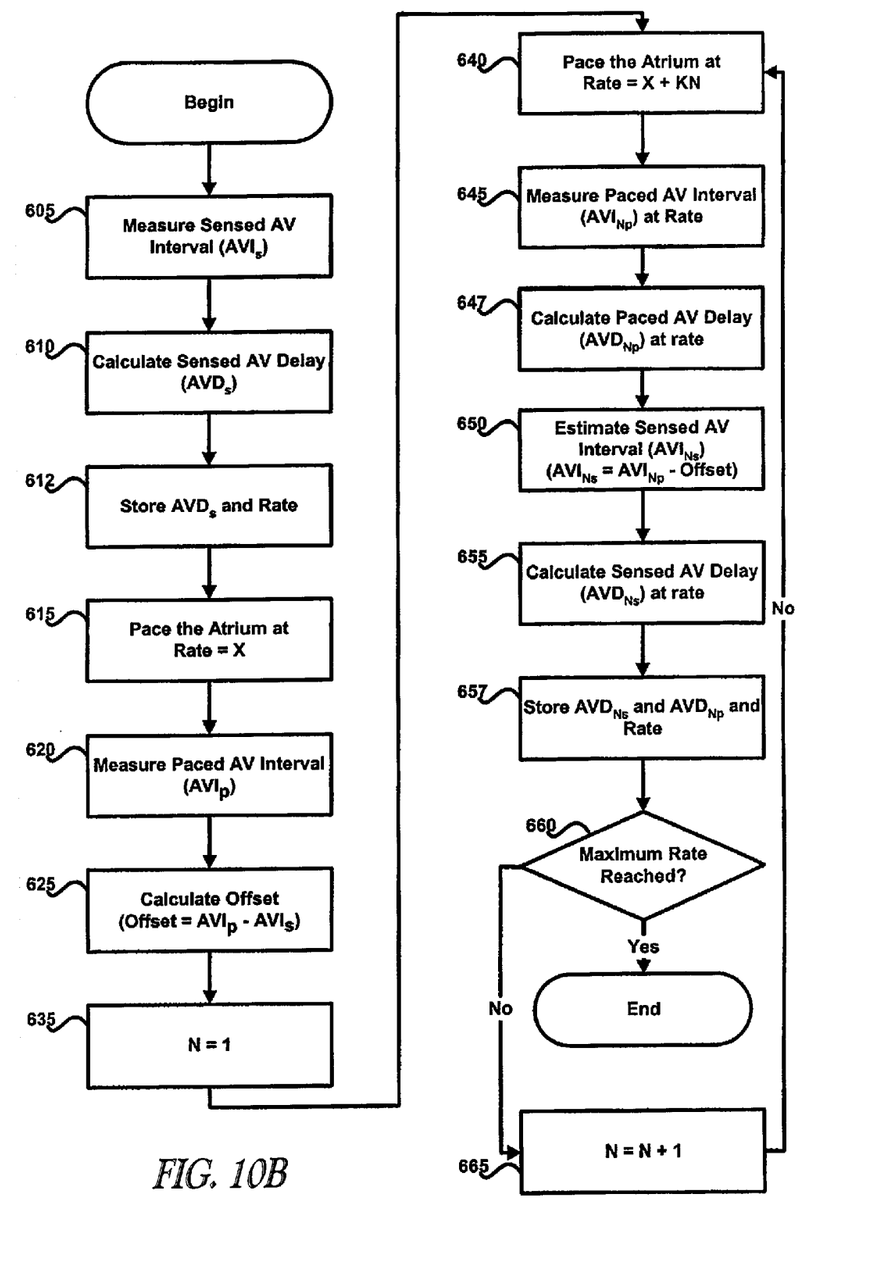
FIG. 10B is another example flow diagram for calculating a plurality of optimized atrioventricular delays for a sensed atrium at a plurality of sensed rates induced by pacing.

Another example method for estimating a plurality of $AVD_s$ at a plurality of atrial pacing rates is shown in FIG. 10B. In operation 605, the $AVI_s$ is measured at a first sensed rate, typically a resting heart rate. Then, in operation 610 the $AVD_s$ is calculated using a known method described above and stored in memory in operation 612. Next, in operation 615, the heart is paced at a rate X slightly higher than the initial sensed rate. In operation 620, the $AVI_p$ is measured, and an offset is calculated in operation 625 using $AVI_p$ and $AVI_s$. See Equation 2 above.

Next, in operation 635 the variable N is set equal to 1, and the atrium is paced at a rate calculated in operation 640 according to Equation 5. Then, in operation 645, the $AVI_{Np}$ is measured for the paced rate, and $AVD_{Np}$ is calculated in operation 647 using a known method as describe above. Next, an $AVI_{Ns}$ is estimated in operation 650 using Equation 6, a modified form of Equation 2.

$$AVI_{Ns} = AVI_{Np} - \text{offset} \qquad (6)$$

Then, in operation 655, an $AVD_{Ns}$ based on the $AVI_{Ns}$ can be calculated using, for example, one or more of the methods described above. The $AVD_{Ns}$ as well as $AVD_{Np}$ and associated rate are stored in operation 657. In operation 660, the CRT device determines whether a maximum pacing rate has been reached. If the maximum rate has been reached, the measurements are complete and the atrial test pacing is ceased. If the maximum rate has not been reached, the variable N is incremented and control is passed back to operation 640 for a new set of measurements and calculation of a new $AVD_{Ns}$ (and $ADV_{Np}$) at a higher pacing rate.

Once all measurements are completed, the CRT device 206 may create a table, such as example Table 3 illustrated below, including the $AVD_{Ns}$ and $AVD_{Np}$ for each pacing rate. A CRT device may utilize such a table to look up an optimal $AVD_s$ or $AVD_p$ depending on the sensed/paced atrial rate. As the atrial sensed or paced rate changes, the CRT device 206 can lookup the appropriate $AVD_s$ or $ADV_p$, thereby maintaining an optimal $AVD_s$ or $AVD_p$ as the sensed or paced rate changes.

TABLE 3

| Pacing Rate | Optimized $AVD_s$ | Optimized $AVD_p$ |
|---|---|---|
| X + KN | $AVD_{Ns}$ | $AVD_{Np}$ |
| X + K(N + 1) | $AVD_{(N+1)s}$ | $AVD_{(N+1)p}$ |
| X + K(N + 2) | $AVD_{(N+2)s}$ | $AVD_{(N+2)p}$ |
| X + K(N + 3) | $AVD_{(N+3)s}$ | $AVD_{(N+3)p}$ |
| X + K(N + 4) | $AVD_{(N+4)s}$ | $AVD_{(N+4)p}$ |
| X + K(N + 5) | $AVD_{(N+5)s}$ | $AVD_{(N+5)p}$ |

IV. Optimization of Sensed AV Delay During Mode Switch Between Atrial Sensing and Pacing Knowing both the $AVD_s$ and $AVD_p$ for a particular patient can be important because a CRT device may undergo a mode switch during use. A mode switch can include a switch from atrial pacing to atrial sensing such as, for example, when a patient changes status from resting to exercising. During such a mode switch from pacing to sensing (or vice versa), the CRT device should switch from the optimized $AVD_p$ to the optimized $AVD_s$ of the CRT device, thereby continuing to maintain an optimized AVD.

Figure 11:
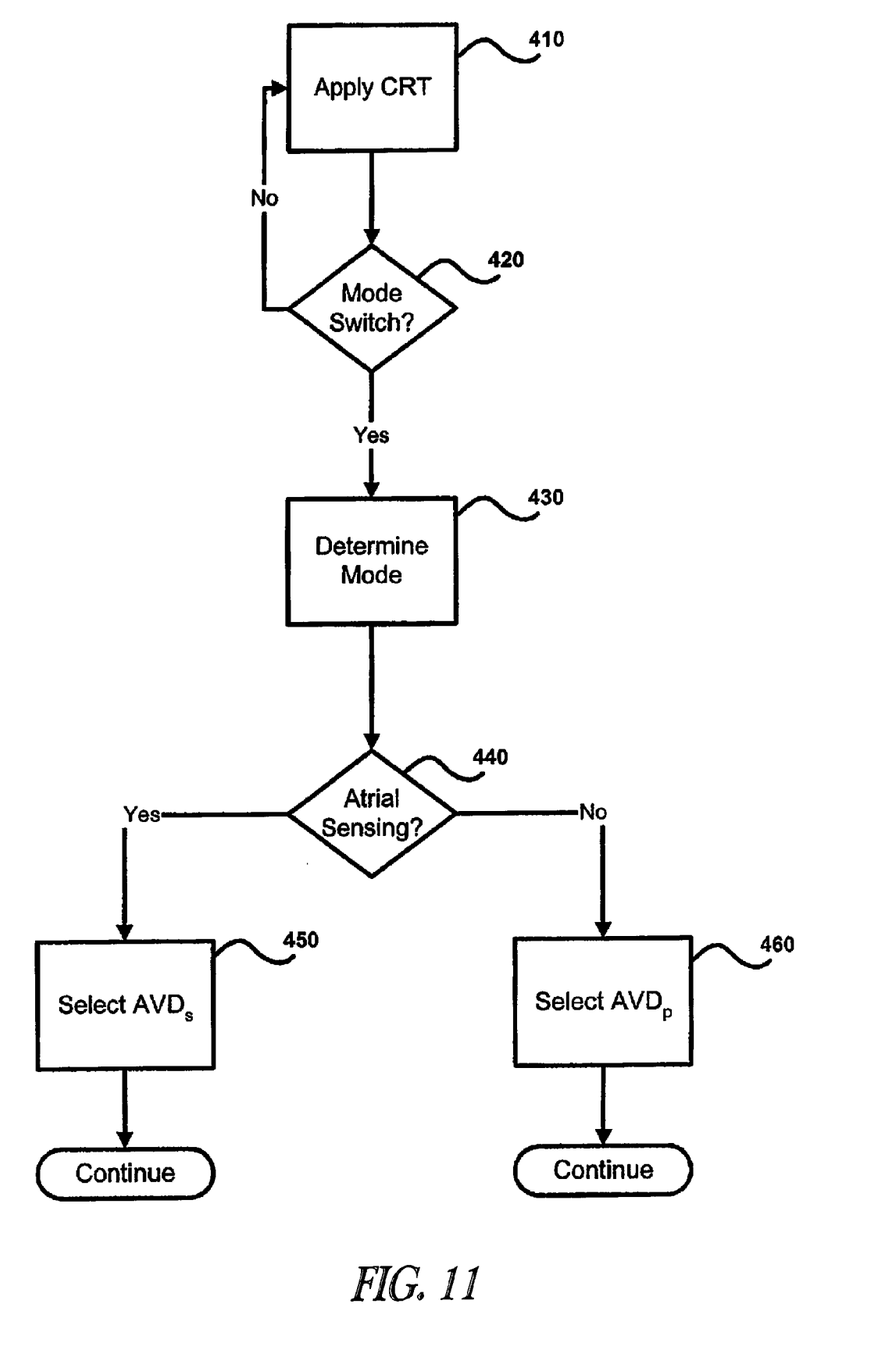
FIG. 11 is an example flow diagram for a cardiac rhythm management system applying optimized sensed and paced atrioventricular delays during a mode switch.

For example, an operation flow for an example CRT device is shown in FIG. 11. In operation 410, CRT is applied to a patient. In operation 420, the CRT device determines if a mode switch has occurred. The mode switch may be from atrial sensing to pacing, or atrial pacing to sensing. If a mode switch has occurred, control is passed to operation 430, wherein the device determines the current mode in which the CRT device is operating. If the CRT device is now operating in atrial sensing mode, control is passed to operation 450 and the optimized $AVD_s$ is selected. Conversely, if the CRT device is now operating in atrial pacing mode, control is passed to operation 460 and the optimized $AVD_p$ is selected. In this manner, AVD may be optimized before and after a mode switch.

Figure 12:
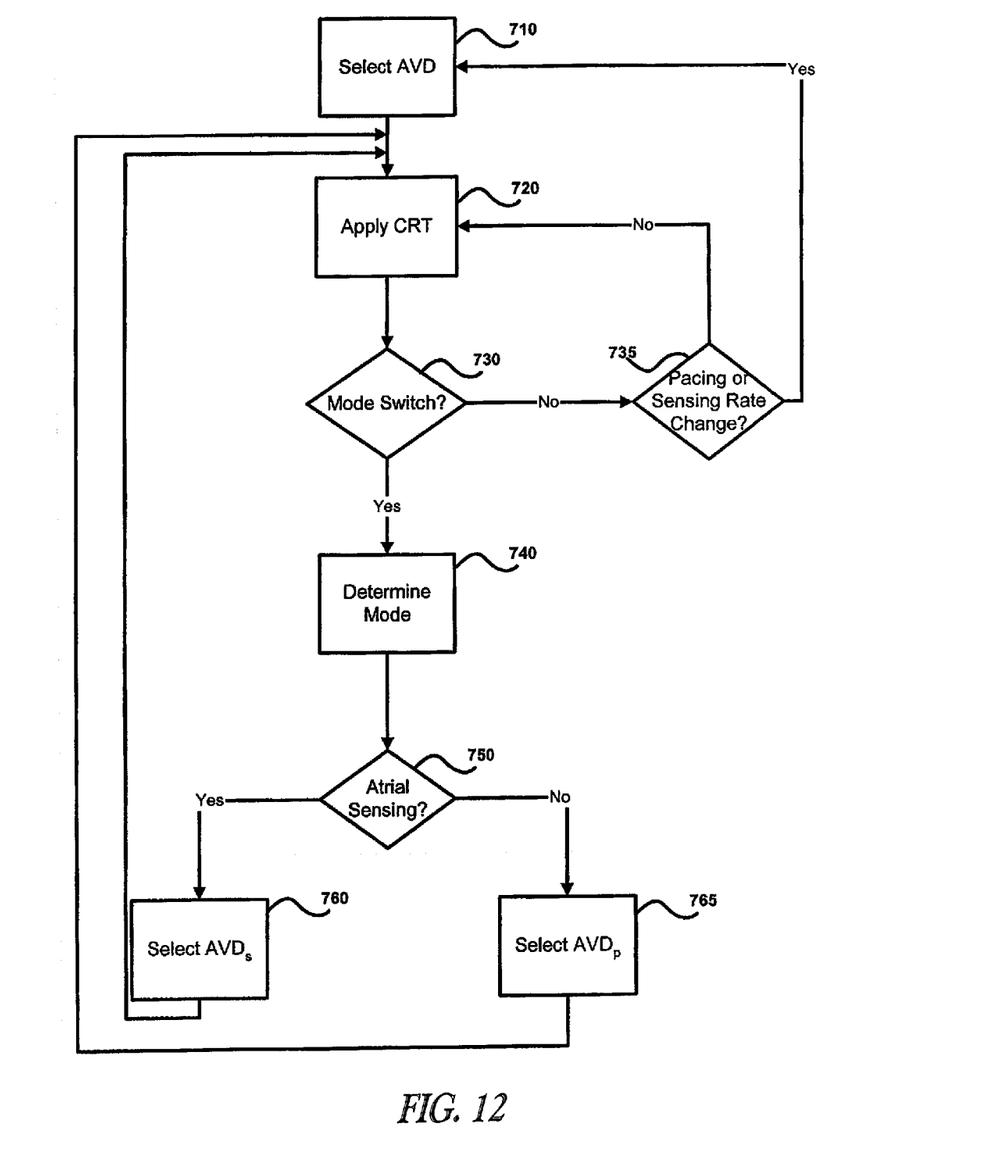
FIG. 12 is an example flow diagram for a cardiac rhythm management system implementing optimized atrioventricular delay for a plurality of pacing rates and for both atrial sensing and pacing modes.

For example, a flow diagram shown in FIG. 12 illustrates how a CRT device may utilize lookup tables including a plurality of $AVD_{Np}$ and $AVD_{Ns}$. In operation 710, an appropriate $AVD_s$ based on a current pacing or sensing rate, is selected. An appropriate AVD is selected, for example, by looking up the AVD in either a pacing lookup table or a sensing lookup table stored on the CRT device. If the CRT is functioning in sensing mode, the current sensed rate is used to select an appropriate $AVD_s$ from the sensing lookup table. Alternatively, if the CRT device is functioning in pacing mode, the current pacing rate is used to select an appropriate $AVD_p$ from the pacing lookup table.

Next, in operation 720, CRT is applied. In operation 730, the CRT device determines whether there has been a mode switch, either from sensing to pacing or from pacing to sensing. If a mode switch has occurred, control is passed to 740, wherein the current mode is determined. If the current mode is sensing, control is passed to operation 760, in which an appropriate $AVD_s$ from the sensing lookup table for the current pacing rate is selected. If the current mode is pacing, control is passed to operation 765, in which an appropriate $AVD_p$ from the pacing lookup table for the current pacing rate is selected. After selecting an appropriate $AVD_s$ or $AVD_p$, control is passed back to operation 720 and CRT continues.

If, in operation 730, the CRT device determines that a mode switch has not occurred, control is passed to operation 735, in which the CRT device determines if the current pacing rate has changed. If the pacing rate has changed, control is passed to operation 710, in which a new AVD is looked up in either the sensing or pacing lookup table. If, in operation 735, the pacing rate has not changed, control is passed back to operation 720 and CRT continues.

V. Alternative Embodiments

The above systems and methods can be modified without departing from the inventive concepts disclosed herein. For example, instead of calculating a plurality of $AVD_s$ at different pacing rates as described in section III above, it may only be necessary to calculate two $AVD_s$, one at a low pacing rate and one at a high pacing rate. Using these two $AVD_s$, it may be possible to interpolate the remaining values, assuming a relationship such as a linear relationship between $AVD_s$ for different sensed rates. In addition, other methods besides those illustrated above can be used to calculate an optimal $AVD_s$ and $AVD_p$.

The logical operations for calculating the optimized $AVD_s$ may be performed by a device other than an implanted CRT device 206. For example, an external device programmer, communicating via telemetry, may be used. Furthermore, the logical operations may be implemented (1) as a sequence of computer implemented steps running on a computer system, and/or (2) as interconnected machine modules.

This implementation is a matter of choice dependent on the performance requirements of the device 206 or device programmer implementing the invention. Accordingly, the logical operations making up the embodiments of the invention described herein are referred to as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

While the invention has been particularly shown and described with reference to preferred embodiments thereof, it will be understood by those skilled in the art that various other changes in the form and details may be made therein without departing from the spirit and scope of the invention.

What is claimed is:

1. A cardiac resynchronization device, comprising:
a therapy module for delivering cardiac resynchronization therapy with a selected atrioventricular delay, wherein the cardiac resynchronization therapy includes delivering ventricular pacing upon expiration of a selected atrioventricular delay $AVD_s$ after an atrial sense and upon expiration of a selected atrioventricular delay $AVD_p$ after an atrial pace;
a sensing module and a timer module capable of sensing and timing a plurality of sensed and paced intrinsic atrioventricular intervals at a plurality of rates, wherein a sensed intrinsic atrioventricular interval is the interval between an atrial sense and a ventricular sense and wherein a paced intrinsic atrioventricular interval is the interval between an atrial pace and a ventricular sense;
a controller coupled to the timer module capable of calculating a plurality of $AVD_s$ values and $AVD_p$ values for use in delivering resynchronization therapy at different atrial rates based on the plurality of atrioventricular intervals;
a memory module capable of storing the plurality of atrioventricular delay values;
wherein the controller is configured to calculate a plurality of different $AVD_s$ values for each of a plurality of a sensed atrial rates by: 1) operating in a ventricular pacing mode with atrial sensing but no atrial pacing, 2) when the currently sensed atrial rate corresponds to one of the plurality of sensed atrial rates, calculating and storing an $AVD_s$ value for that sensed atrial rate as a function of the intrinsic atrioventricular interval, 3) storing each calculated $AVD_s$ value with an associated specified expiration interval so that the $AVD_s$ value expires after the expiration interval lapses, 4) when the currently sensed atrial rate corresponds to one of the plurality of sensed atrial rates for which the $AVD_s$ value has been previously calculated but has expired, recalculating and storing the $AVD_s$ value for that sensed atrial rate;
wherein the controller is configured to calculate a plurality of different $AVD_p$ values for each of a plurality of a paced atrial rates by: 1) operating in a ventricular pacing mode with atrial pacing, 2) varying the atrial pacing rate to corresponds to each of the plurality of paced atrial rates, and 3) calculating and storing an $AVD_p$ value for each paced atrial rate as a function of the intrinsic atrioventricular interval measured at each particular atrial pacing rate; and,
wherein the controller is configured to automatically select one of the plurality of stored $AVD_s$ values and $AVD_p$ values based on an interval between atrial beats of consecutive cardiac cycles.

2. The cardiac resynchronization device of claim 1, wherein the controller is further configured to automatically select one of the plurality of atrioventricular delay values based on a current sensed rate after switching from a ventricular pacing mode with atrial pacing to a ventricular pacing mode with no atrial pacing.

3. The cardiac resynchronization device of claim 1, wherein the controller is further configured to automatically select one of the plurality of atrioventricular delay values based on a current pacing rate after switching from a ventricular pacing mode with no atrial pacing to a ventricular pacing mode with atrial pacing.

4. The cardiac resynchronization device of claim 1, wherein the controller is further configured to pace the heart at increasing rates, wherein the sensing module and timer module are capable of sensing and timing a paced atrioventricular interval at each increased pacing rate, and wherein the controller is capable of calculating the plurality of atrioventricular delay values based on the associated paced atrioventricular interval.

5. The cardiac resynchronization device of claim 1, wherein the controller is configured to determine whether a previous value has been calculated or has expired for the plurality of atrioventricular delay values.

6. The cardiac resynchronization device of claim 5, wherein an atrioventricular delay value is stored in the memory if the previous value has not been calculated or has expired.

7. The cardiac resynchronization device of claim 1, wherein the controller is further configured to automatically select between a sensed atrioventricular delay and a paced atrioventricular delay based on a mode in which the cardiac resynchronization device is operating.

8. The cardiac resynchronization device of claim 1 wherein the device is configured to:

calculate an $AVD_s$ value for a particular atrial rate as a function of a sensed intrinsic atrioventricular interval $AVI_s$ measured at that particular atrial rate as $AVD_s = K1(AVI_s) - K2$; and, calculate an $AVD_p$ value for a particular atrial pacing rate as a function of a paced intrinsic atrioventricular interval $AVI_p$ measured at that particular atrial pacing rate as $AVD_p = K1(AVI_p) - K2$.

9. The cardiac resynchronization device of claim 1 wherein the device is configured to increase the atrial pacing rate through a range of different pacing rates in order to collect paced intrinsic atrioventricular intervals at different atrial pacing rates and calculate corresponding $AVD_p$ values.

10. The cardiac resynchronization device of claim 1 wherein the device is configured to opportunistically calculate corresponding $AVD_s$ values as atrial senses occur and subsequently increase the atrial pacing rate by a specified amount above the intrinsic atrial rate to calculate an $AVD_p$ value.

* * * * *